United States Patent

Harvie

(10) Patent No.: US 10,106,444 B2
(45) Date of Patent: Oct. 23, 2018

(54) VITALITY STICK SYSTEM AND METHOD

(71) Applicant: Sheila Erin Harvie, Nanton (CA)

(72) Inventor: Sheila Erin Harvie, Nanton (CA)

(73) Assignee: Sheila Erin Harvie, Nanton, Alberta (CA)

( * ) Notice: Subject to any disclaimer, the term of this patent is extended or adjusted under 35 U.S.C. 154(b) by 226 days.

(21) Appl. No.: 15/269,918

(22) Filed: Sep. 19, 2016

(65) Prior Publication Data

US 2018/0079666 A1  Mar. 22, 2018

(51) Int. Cl.
| | |
|---|---|
| A61K 33/00 | (2006.01) |
| A61K 33/26 | (2006.01) |
| A61K 33/34 | (2006.01) |
| A61K 33/38 | (2006.01) |
| A61K 33/44 | (2006.01) |
| C02F 1/28 | (2006.01) |
| C02F 1/48 | (2006.01) |
| C02F 1/50 | (2006.01) |
| C02F 1/68 | (2006.01) |
| A61K 33/32 | (2006.01) |

(Continued)

(52) U.S. Cl.
CPC .............. *C02F 1/685* (2013.01); *A61K 33/00* (2013.01); *A61K 33/26* (2013.01); *A61K 33/32* (2013.01); *A61K 33/34* (2013.01); *A61K 33/38* (2013.01); *A61K 33/44* (2013.01); *C02F 1/005* (2013.01); *C02F 1/283* (2013.01); *C02F 1/48* (2013.01); *C02F 1/505* (2013.01); *C02F 2103/026* (2013.01); *C02F 2305/08* (2013.01); *C02F 2307/02* (2013.01)

(58) Field of Classification Search
CPC ........ A61K 33/00; A61K 33/26; A61K 33/32; A61K 33/34; A61K 33/38; A61K 33/44; C02F 1/005; C02F 1/283; C02F 1/48; C02F 1/505; C02F 1/685; C02F 1/687; C02F 1/688; C02F 2103/026; C02F 2305/08; C02F 2307/02
See application file for complete search history.

(56) References Cited

U.S. PATENT DOCUMENTS

| | | | |
|---|---|---|---|
| 4,447,254 A | 5/1984 | Hughes et al. | |
| 5,013,417 A | 5/1991 | Judd, Jr. | |

(Continued)

FOREIGN PATENT DOCUMENTS

| | | | |
|---|---|---|---|
| CN | 2086162 U | * | 10/1991 |
| CN | 203683153 U | * | 7/2014 |
| CN | 204661447 U | * | 9/2015 |

OTHER PUBLICATIONS

Machine Translation of CN 2086162 U (obtained from google patents Jun. 2018) (Year: 1991).*

(Continued)

*Primary Examiner* — Lucas A Stelling

(57) ABSTRACT

A device for affecting water. The device for affecting water includes a first-end, a second-end, a length from the first end to the second-end and an extruded member. Gemstones, which generate a pleasant subliminal functional aesthetic, and visible messages, which may have positive neurological and meta-physical effects, are included. The device for affecting water is useful for providing trace mineral elements to humans and animals and for producing positive changes to the overall physical health and emotional well-being of a user.

19 Claims, 5 Drawing Sheets

(51) Int. Cl.
    *C02F 1/00*         (2006.01)
    *C02F 103/02*     (2006.01)

(56)            References Cited

U.S. PATENT DOCUMENTS

| | | | | |
|---|---|---|---|---|
| 6,013,180 | A * | 1/2000 | Wang | C02F 1/003 |
| | | | | 210/232 |
| 6,197,193 | B1 | 3/2001 | Archer | |
| 2002/0008062 | A1 | 1/2002 | Torigoe | |
| 2005/0252844 | A1* | 11/2005 | Chau | C02F 1/002 |
| | | | | 210/282 |
| 2007/0068863 | A1* | 3/2007 | Liu | C02F 1/003 |
| | | | | 210/282 |
| 2007/0221556 | A1* | 9/2007 | Chung | C02F 1/003 |
| | | | | 210/198.1 |
| 2009/0039006 | A1* | 2/2009 | Chung | C02F 1/002 |
| | | | | 210/226 |
| 2010/0012193 | A1* | 1/2010 | Anson | C02F 1/002 |
| | | | | 137/1 |
| 2012/0017766 | A1* | 1/2012 | Anson | C02F 1/688 |
| | | | | 99/290 |
| 2012/0325735 | A1 | 12/2012 | Dicks et al. | |
| 2014/0158640 | A1* | 6/2014 | Elliott | C02F 1/50 |
| | | | | 210/764 |

OTHER PUBLICATIONS

Machine Translation of CN 203683153 U (obtained from google patents Jun. 2018) (Year: 2014).*
Machine Translation of CN 204661447 U (Year: 2015).*
"IMHL students win Grand Challenges Canada Grant" by McGill Staff Reporter, 2013. (Year: 2013).*

\* cited by examiner

VITALITY STICK SYSTEM AND METHOD

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of providing trace minerals, and elements to benefit overall physical health and metaphysical well-being to humans and animals and more specifically relates to a vitality stick system.

2. Description of Related Art

The composition of the human body includes approximately 70% water and approximately 6% minerals such as salts and metals including sodium, calcium, potassium, and iron. Maintaining proper hydration and mineral levels is an important daily activity. Many people drink only water and do not consider adding supplemental mineral ingredients that are beneficial to both mental and physical wellness. A suitable solution is desired.

Several attempts have been made to solve the above-mentioned problems such as those found in U.S. Pat. No. 4,447,254 to Hughes, et al.; U.S. Pat. No. 6,197,193 to Archer; U.S. Pat. No. 5,013,417 to Judd, Jr.; 2002/0008062 to Torigoe; 2012/0325735 to Dicks, et al. and Chinese Pat. No. 2,086,162 to Ye; 203,683,153 to Liangui, et al.; and 204,661,447 to High. This art is representative of providing trace mineral elements to humans. However, none of the above inventions and patents, taken either singly or in combination, is seen to describe the disclosure as claimed.

BRIEF SUMMARY OF THE INVENTION

In view of the foregoing disadvantages inherent in the known providing trace mineral elements to humans art, the present invention provides a novel vitality stick system. The general purpose of the present invention, which will be described subsequently in greater detail is to provide a vitality stick system.

A device for affecting water is disclosed herein. The device for affecting water includes a first-end, a second-end, a length from the first end to the second-end and an extruded member. The extruded member is at least partially made of copper and extends between the first-end and the second-end. The extruded member has a substantially constant cross-sectional perimeter that is perpendicular to the length between the first-end and the second-end. In addition, the cross-sectional perimeter has an isosceles triangle shape, with the isosceles triangle shape further having a base and a height.

According to another embodiment, a device for affecting water is also disclosed herein. The device for affecting water includes a first-end, a second-end, a length from the first-end to the second-end and an extruded member at least partially made of copper extending between the first-end and the second-end. The extruded member has a substantially constant cross-sectional perimeter perpendicular to the length between the first-end and the second-end. Further the cross-sectional perimeter has an isosceles triangle shape, with the isosceles triangle shape having a base and a height. The length of the extruded member is approximately 5 inches in length and the constant cross-sectional perimeter is approximately ¾ inches in width. The extruded member is configured to be able to be removably-inserted within the inner volume of a standard disposable water bottle, and alternatively a reusable beverage vessel, without interfering with a closure mechanism of the standard disposable water bottle, and alternatively the reusable beverage vessel.

The device for affecting water further includes an interlaced mesh structure. The interlaced mesh structure includes a mineral receptacle, and the mineral receptacle includes an interlaced mesh structure that is configured to permit potable water to flow into and out of the mineral receptacle. The mineral receptacle is further configured to be accessible by a user to removably-insert mineral compositions into the mineral receptacle. The mineral compositions are configured to leach mineral trace elements into the potable water when exposed to the potable water. The mineral compositions are selected from a group of mineral compositions consisting of activated coconut carbon, ionic silver nanoparticle balls, tourmaline, shungite, silica-centered microclusters, and mai-fan stone, and the mineral compositions include at least one of activated coconut carbon, ionic silver nanoparticle balls, tourmaline, silica-centered microclusters, shungite, and alternatively maifan stone.

In continuing to refer to the device for affecting water, the first-end, the second-end, and the interlaced mesh structure are integrated with the extruded member, and the first-end and the second-end are each configured to be hollow in cross section, which is able to provide a larger leaching surface area. In addition, the first-end and the second-end each include at least one aligned bipolar magnet.

In referring to the first-end, the device for affecting water further includes at least one gemstone with the at least one gemstone having a pleasant subliminal functional aesthetic. The at least one gemstone includes at least one clear crystal quartz, amethyst, blue sodalite, green fluorite, rose crystal quartz, and alternatively calcite-gemstone, and the least one gemstone is able to be selected from a group consisting of clear crystal quartz, amethyst, blue sodalite, green fluorite, rose crystal quartz, and calcite-gemstone. In addition, the at least one gemstone further includes a mounting interface configured to fixedly-attach, and alternatively to removably-couple, at least one gemstone to the first-end. In further referring to the second-end, the second-end includes visual indicia that is able to promote a positive emotional response for a user viewing the visual indicia. The visual indicia includes at least one word, at least one image, and alternatively at least one word and at least one image in combination, that is able to induce a subliminal sentiment associated therewith for the user.

According to an alternative embodiment disclosed herein, the extruded member includes a solid cross section, and the mineral receptacle is vacated from the extruded member, and the mineral composition is able to be sufficient to continue leaching mineral trace elements into potable water for an extended period of time.

According to an alternative embodiment disclosed herein, the extruded member includes first-copper shell, a second-copper shell, a third-copper shell, a fourth-copper shell, and a fifth-copper shell with a first-mesh structure situated between the first-copper shell and the second-copper shell, a second-mesh structure situated between the second-copper shell and the third-copper shell, a third-mesh structure situated between the third-copper shell and the fourth-copper shell, and a fourth-mesh structure situated between the fourth-copper shell and the fifth-copper shell in structural and functional combination to create a plurality of interlaced mesh structures in alternating configuration with an outer copper shell that is configured to permit potable water to flow into and out of the extruded member.

According to another embodiment, a device for affecting water is also disclosed herein. The method of use for a device for affecting water includes placing a mineral composition in the mineral receptacle; inserting the device for affecting water in a standard disposable water bottle, and alternatively a reusable beverage vessel; removing the device for affecting water from the standard disposable water bottle, and alternatively the reusable beverage vessel, when use is no longer desired; replacing at least one gemstone with another at least one gemstone when a different aesthetic is desired; and viewing a visual indicia to induce a subliminal sentiment associated therewith.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a device for affecting water, constructed and operative according to the teachings of the present disclosure.

The various embodiments of the present invention will hereinafter be described in conjunction with the appended drawings, wherein like designations denote like elements.

DETAILED DESCRIPTION

Figure 1:
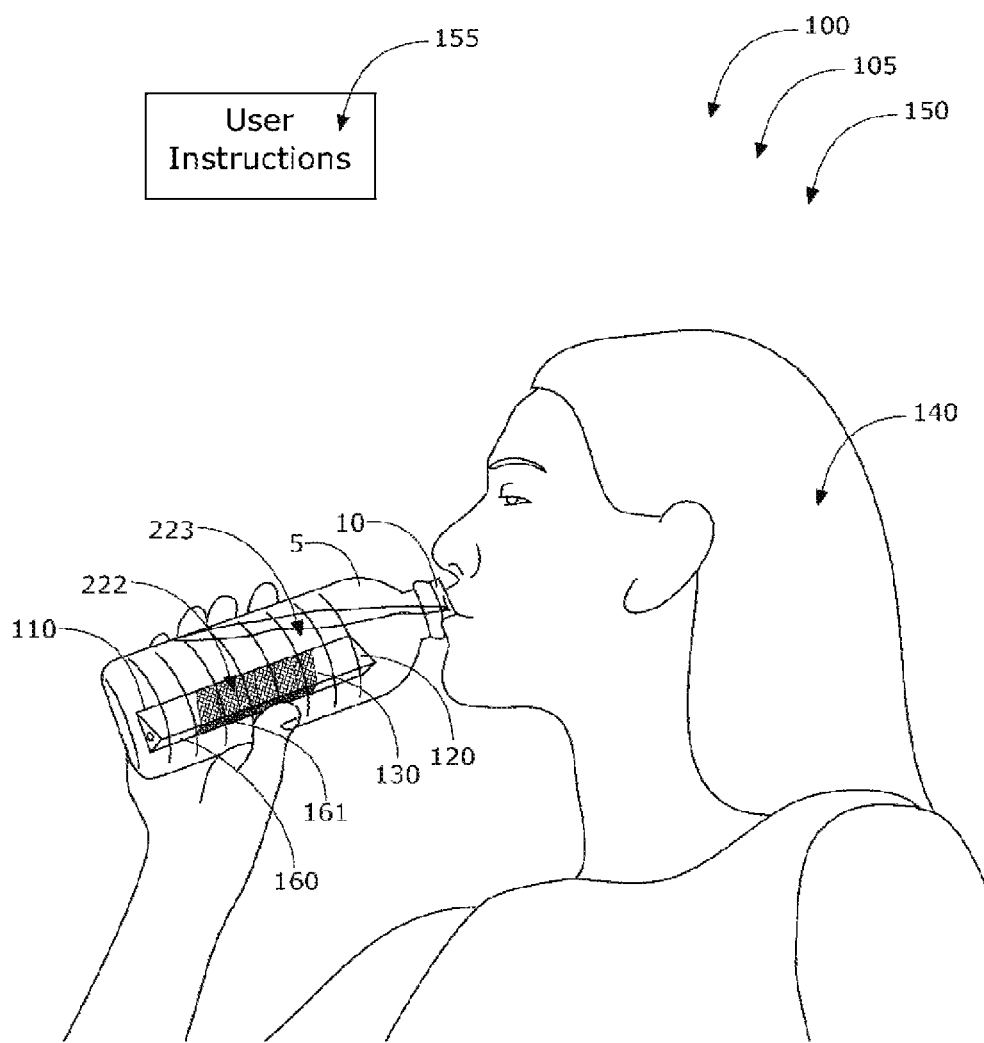
FIG. 1 shows a side view illustrating a device for affecting water during an 'in-use' condition according to an embodiment of the disclosure.

As discussed above, embodiments of the present disclosure relate to a providing trace mineral elements to humans and more particularly to a vitality stick system as used to improve a device for affecting water.

Generally speaking, the human body is made of 70% water, so the quality of water that is ingested is very important to overall physical health and metaphysical well-being. The present inventor is using the premise that high-speed photography can capture the structure of water at the moment of freezing. This frozen crystalline structure has been correlated with a response to a person's thoughts to explore the consequences of destructive thoughts, as well as thoughts of positivity, love, and appreciation, during the formation of the water crystals. The present inventor is using the premise that thoughts can influence water, which may have profound implications for health and well-being. The natural resonant frequency of water (and all organic organisms) is within the far infrared (FIR) frequency band. Water is both a receiver and an emitter of the FIR frequency band. It vibrates vigorously at these wavelengths and FIR wavelengths between 4 and 16 microns play an important role in overall health. FIR resonance absorption may improve vitality of living tissues, enhance energy levels and increase metabolism.

The vitality stick, or energy stick, provides an environmentally-friendly, 3-dimensional, triangle-shaped copper-based stick that enhances properties of daily drinking water and boosts overall health and vitality. The copper stick may be produced in a variety of shapes which may include a heart shape or an infinity sign which may resemble a FIG. 8. The shapes may further include geometric shapes or geometric proportions of forms found in nature that are considered to be "sacred geometry" forms. When added to drinking water, the copper stick beneficially-increases the alkalinity of the water. The auyervedic benefits of copper consumption may include boosting anti-inflammatory, anti-bacterial, anti-microbial, anti-oxidant, anti-carcinogenic, and pro-melanin agents in the human body. It is possible that the aforementioned benefits may be applied to animals and animal drinking water, as well.

The vitality stick includes mesh compartments that provide for retention and controlled release of trace elements. The trace elements can include, but are not limited to a variety of combinations of vitamins, minerals, silica-centered microclusters, calcium, iron, magnesium, potassium, sodium, zinc and other trace minerals, and the like, in the form of ionic mineral balls/stones. Some of the ionic mineral balls/stones are made of highly porous mineral stones to aid in changing the oxygenation alkalinity of the water. The ionic mineral balls/stones can continuously release health enhancing ionized (bioavailable) minerals while they gradually deplete in size for a period of up to 5 years depending on usage frequency. The quantity and composition of ionic mineral balls/stones included in the vitality stick may also vary to allow for customization.

More specifically, the ionic mineral balls/stones may be targeted to include activated coconut carbon, ionic silver nanoparticle balls, tourmaline, shungite, silica-centered microclusters, and maifan minerals. The activated coconut carbon may be made from high-quality coconut shells. Activated coconut carbon is believed to be able to neutralize and remove chlorine, chloramines, heavy metals, industrial chemicals, and agricultural chemicals from water. It may further decompose noxious compounds and organics such as hydrogen sulfide and chloramine while neutralizing undesirable tastes and odors found in drinking water. Ionic silver nanoparticle balls are believed to be able to eliminate bacterial infections and speed tissue repair and growth. In a naturally charged state ionic silver nanoparticle balls may encourage production of stem cells, and cause fibroblast organisms to alter their normal cellular morphology to destroy, remove, or otherwise render fibroblast organisms ineffective as infection causing agents in the body. It is believed that the ionic silver nanoparticle balls may be able to penetrate the cell walls of viruses and/or bacteria to inhibit cellular respiration and/or reproduction. The use of maifan minerals originated in Chinese medicine practices. Maifan minerals contain micro-nutrient elements such as calcium, iron, zinc, magnesium, copper, and selenium, which are all essential to a maintain a healthy human body.

Use of tourmaline beneficially increases water alkalinity, reduces water clustering, and has anti-bacterial and deododarizing qualities to enhance water taste. Electric current flows through tourmaline via movement of electrons that originated from the sun, with negatively-charged electrons entering the positively-charged side of tourmaline and exiting from the negatively-charged side. With this current flow, tourmaline is like a battery with unlimited life. When placed in water, slight pressure contributes to the piezoelectric effect that supports water's crystalline structure with a slight positive charge. Because the FIR rays emitted by tourmaline create the same resonance in the body as water, tourmaline has a soothing effect on nerves. Tourmaline is also known for its ability to aid in the detoxification process and for balancing metabolic functions.

Shungite contains many of the minerals in the periodic table and is useful for harmonizing energy, for blocking electromagnetic field (EMF) and geopathic stress effects, and for creating good health and a healthy immune system. Shungite transforms water into a biologically active life-enhancing substance, while removing harmful micro-organisms and pollutants by absorbing elements that are hazardous to health such as pesticides, free radicals, bacteria and the like, or EMF, microwave, and other vibrational emissions. It is believed that shungite infused water consumed several times a day may eliminate free radicals and pollutants and act as an antibacterial and antiviral element, which may reduce the intensity and duration of the common cold and other diseases.

Silica-centered microclusters may contribute to increased bio-availability for the body's absorbtion of nutrients at a cellular level while simulataneously improving the absorption and effectiveness of food- and supplement-nutritional value(s). In addition, silica-centered microclusters superhydrate these nutrients, which may beneficially-increase overall human hydration levels. Further, silica-centered microclusters may assist in the body's natural detoxification and elimination processes. Also, silica-centered microclusters may assist in creating negatively-charged hydrogen ions which aid in neutralizing harmful free-radicals in the body. Ultimately silica-centered microclusters may enhance drinking water's benefits to compare to the benefits realized from the purest mountain spring waters.

The vitality stick will also include a pair of aligned bipolar magnets that will be embedded in the visible outer surface of the copper at either end of the stick. Continued use of aligned bipolar magnets may improve overall metabolic levels and boost energy, and potentially alleviate colds, coughs, bronchitis, and/or fever. Aligned bipolar magnets may also be able to break up kidney and gallbladder stones into small pieces.

The vitality stick may also be configured to include any type of gemstone. For example, the following gemstones, each believed to have unique health and vitality improving qualities, may be included: clear quartz crystal (may increase the efficacy of other crystals while increasing awareness, neutrality, perception, attention, memory, and understanding, while harmonizing the brain, nerves, glands, and hormones. It may distribute energy and alleviate pain, while improving the appearance of skin, hair, and nails); amethyst (may increase the positive effects of other crystals and promote clarity, awareness, neutrality, and a firm standpoint, as well as strengthen perception, attention, memory, and understanding by harmonizing the brain, nerves, and glands, while balancing hormones. Further, amethyst may generate energy and alleviate pain, while improving the appearance of skin, hair, and nails); blue sodalite (may promote awareness, striving for truth, idealism, and being true to ones self. It may be beneficial to the throat, larynx, vocal chords, kidneys, and bladder. It also may have a fever-abating effect and may increase absorption of fluids).

Green fluorite (may promote sense of order, self-determination, flexibility, and a free spirit. It may encourage increased concentration, thinking, and learning while promoting clarity of thought. It may strengthen teeth and bones, and reduce ganglions and joint pain. It may be good for the skin, mucous membranes, respiratory system, lungs, intestines, nerves, and the brain. It may also alleviate the effects of allergies); rose quartz (may promote feelings of affection, empathy, directness, sensitivity, sensuality, and romance. It may promote awareness of one's own needs. It may strengthen the heart, circulatory system, and reproductive organs to include increasing fertility in women. It may also improve skins tone and texture); and calcite (may promote stability, steadfastness, self confidence, healthy growth, and harmonious development. It may reduce the tendency to be lazy, strengthen the ability to overcome difficulties, and make a person feel capable and successful. It may also regulate metabolism, digestion, and waste elimination. It may have benefits for bones, teeth, connective tissue, skin, mucous membranes, and intestines).

Further, positive neurological effects may be gained by adding visible positive messages on the vitality stick. A selection of positive messages may include, at a minimum, the following words and phrases: "Love"; "Aspire to Inspire"; "Attitude of Gratitude"; "Freedom"; "Go with the Flow"; "Energize"; "Balance"; "Happiness is an Attitude"; "Keep Moving Forward"; "Breathe Deeply"; "Peace"; "Courage"; "Live in the Moment"; "Shine Bright"; "Pursue your Dreams"; "Be Fearless"; "Take Chances"; "Create Happiness"; "Be Passionate"; "Laugh Every Day"; "Be Generous"; or "Practice Kindness". The present inventor is using the premise that water changes its crystal structure in response to a person's reaction to positive words and messages. Inclusion of visible positive messages and symbols on the vitality stick can serve to initiate the water's reaction to support improved health and well-being.

Referring now more specifically to the drawings by numerals of reference, there is shown in FIGS. 1-4, various views of a device for affecting water 100. FIG. 1 shows a device for affecting water during an 'in-use' condition 150, according to an embodiment of the present disclosure. Here, the device for affecting water may be beneficial for use by a user 140 to providing trace mineral elements to humans. As illustrated, the device for affecting water 100 may include first-end 110, second-end 120, length 130 from first-end 110 to second-end 120, and extruded member 160. Extruded member 160 may be at least partially made of copper 161 and extend between first-end 110 and second-end 120. Extruded member 160 may be configured to be able to be removably-inserted within an inner volume of standard disposable water bottle 5, and alternatively reusable beverage vessel 15, without interfering with closure mechanism 10 of standard disposable water bottle 5, and alternatively reusable beverage vessel 15. In an alternate use of the present invention, reusable beverage vessel may include a glass, multi-serving beverage dispenser. Extruded member 160 may be configured to retain mineral compositions 222 that may distribute mineral trace elements 223 to user 140 desiring to receive benefits of consumption of mineral trace elements 223.

According to one embodiment, the device for affecting water 100 may be arranged as a kit 105. In particular, the device for affecting water 100 may further include a set of instructions 155. The instructions 155 may detail functional relationships in relation to the structure of the device for affecting water 100 (such that the device for affecting water 100 can be used, maintained, or the like, in a preferred manner).

Figure 2:
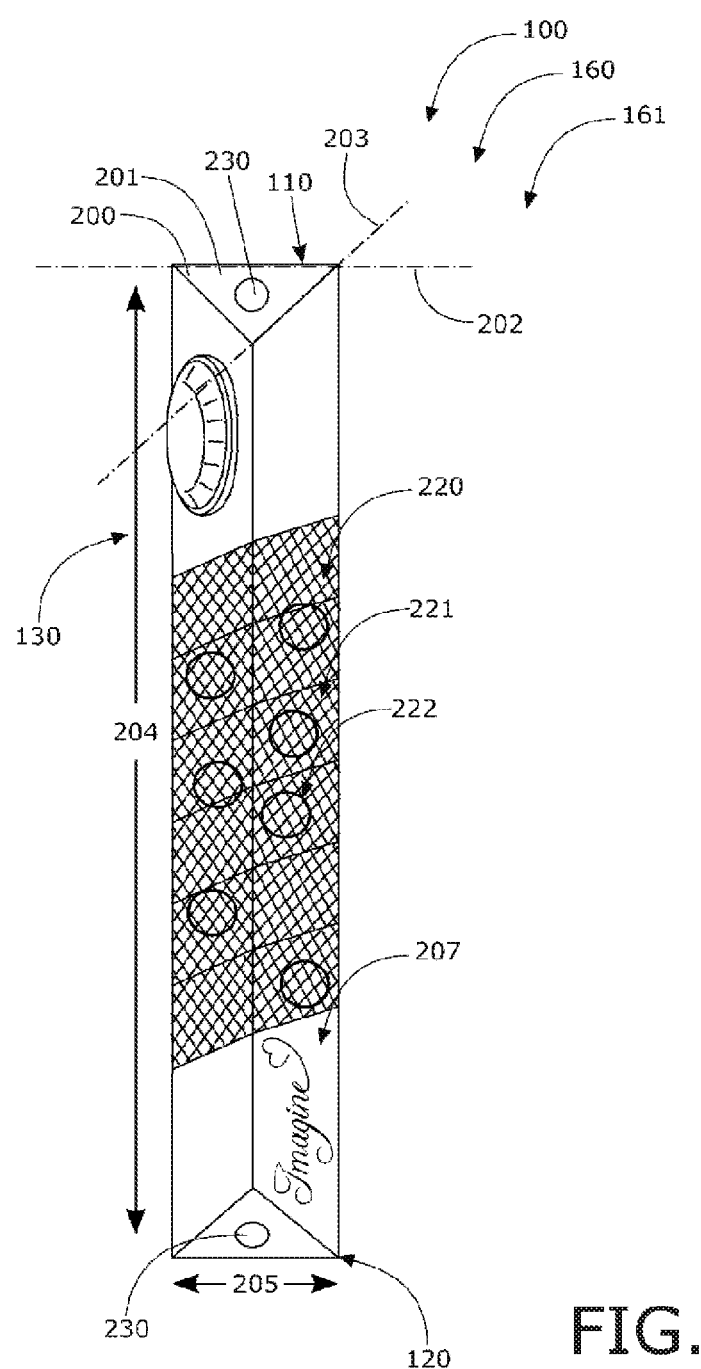
FIG. 2 is a top view illustrating the device for affecting water of FIG. 1, according to an embodiment of the present invention of the disclosure.

FIG. 2 shows the device for affecting water of FIG. 1, according to an embodiment of the present disclosure. As above, the device for affecting water 100 may include first-end 110, second-end 120, length 130 from first-end 110 to second-end 120 and extruded member 160 at least partially made of copper 161 extending between first-end 110 and second-end 120. Extruded member 160 may have a substantially constant cross-sectional perimeter 200 perpendicular to length 130 between first-end 110 and second-end 120. In addition, substantially constant cross-sectional perimeter 200 may have isosceles triangle shape 201, with isosceles triangle shape 201 further having a base 202 and a height 203. Length 130 of extruded member 160 may be approximately 5 inches in length 204 and substantially constant cross-sectional perimeter 200 may be approximately ¾ inches in width 205.

In continuing to refer FIG. 2, extruded member 160 may include interlaced mesh structure 220. Interlaced mesh structure 220 further may include mineral receptacle 221, and mineral receptacle 221 with interlaced mesh structure 220 may be further configured to permit potable water 20 (FIG. 1) to flow into and out of mineral receptacle 221. Mineral receptacle 221 may be configured to be accessible by user 140 (FIG. 1) to removably-insert mineral compositions 222 into mineral receptacle 221 with mineral composition 222 configured to leach mineral trace elements 223 (FIG. 1) into potable water 20 (FIG. 1) when exposed to potable water 20 (FIG. 1). Mineral composition may be selected from a group of mineral compositions 222 consisting of activated coconut carbon 300, ionic silver nanoparticle balls 301, tourmaline 310, shungite 311, silica-centered microclusters 303, and maifan stone 302, and mineral composition 222 further may include at least one of activated coconut carbon 300, ionic silver nanoparticle balls 301, tourmaline 310, shungite 311, silica-centered microclusters 303, and alternatively maifan stone 302.

In further referring to FIG. 2, first-end 110, second-end 120, and interlaced mesh structure 220 are integrated with extruded member 160. In addition, first-end 110 and second-end 120 are each configured to be hollow in cross section 206, which may provide for a larger leaching surface area 207. In addition, first-end 110 and second-end 120 each include at least one aligned bipolar magnet 230. According to an alternate embodiment for device for affecting water 100 disclosed herein, extruded member 160 may have a solid cross section 208, mineral receptacle 221 may be vacated from extruded member 160, and mineral composition 222 may be sufficient to continue leaching mineral trace elements 223 (FIG. 1) into potable water 20 (FIG. 1) for an extended period of time.

Figure 3A:
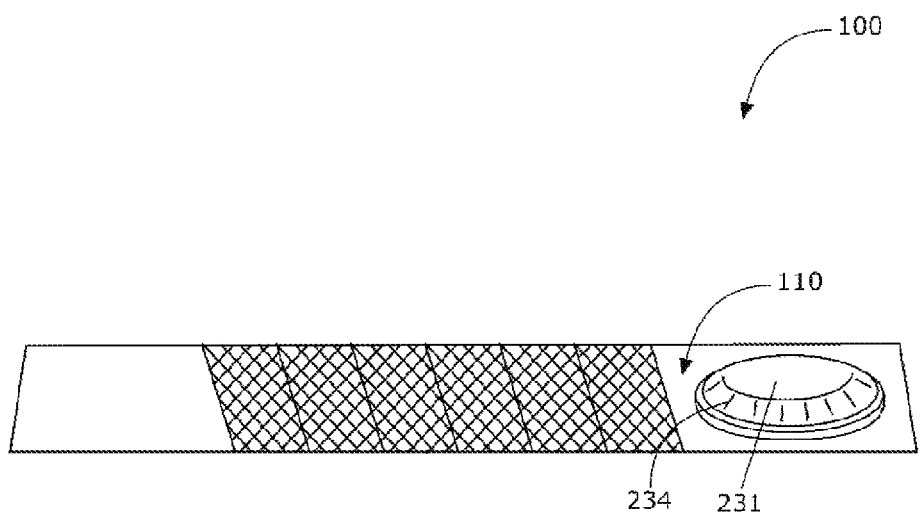
FIG. 3A is a side view illustrating the device for affecting water of FIG. 1, according to an embodiment of the present disclosure.
Figure 3B:
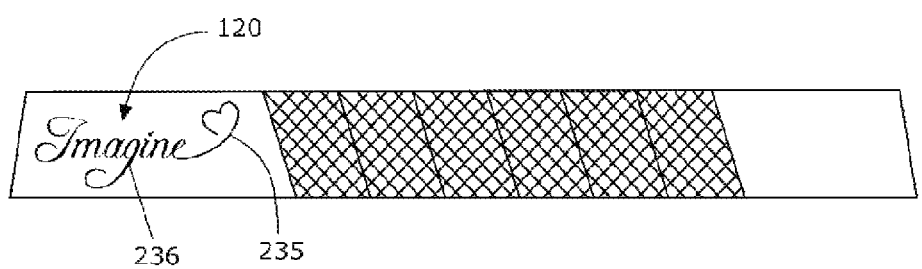
FIG. 3B is another side view illustrating the device for affecting water of FIG. 1, according to an embodiment of the present disclosure.

FIGS. 3A and 3B are side views of the device for affecting water of FIG. 1, according to an embodiment of the present disclosure. In referring now to FIG. 3A, first-end 110 of device for affecting water 100 may include at least one gemstone 231, with at least one gemstone 231 having a pleasant subliminal functional aesthetic. Further, a plurality of at least one gemstones 231 may be alternatively affixed to both first-end 110 and second-end 120 (FIG. 2) of device for affecting water 100. The at least one gemstone 231 may include at least of one clear crystal quartz 312, amethyst 313, blue sodalite 314, green fluorite 315, rose crystal quartz 316, and alternatively calcite-gemstone 317, and least one gemstone 231 may be able to be selected from a group consisting of clear crystal quartz 312, amethyst 313, blue sodalite 314, green fluorite 315, rose crystal quartz 316, and calcite-gemstone 317. In addition, at least one gemstone 231 further may include a mounting interface 234 configured to fixedly-attach, and alternatively to removably-couple, at least one gemstone 231 to first-end 110. In alternate embodiments of the present invention, other types of gemstones may be optionally used.

In referring now to FIG. 3B, second-end 120 of device for affecting water 100, may include visual indicia 235 that may be able to promote a positive emotional response for user 140 (FIG. 1) viewing visual indicia 235. Visual indicia 235 may include at least one word 236, and alternatively at least one image 237, and alternatively at least one word and at least one image in combination, that may be able to induce a subliminal sentiment associated therewith for user 140 (FIG. 1).

Figure 4:
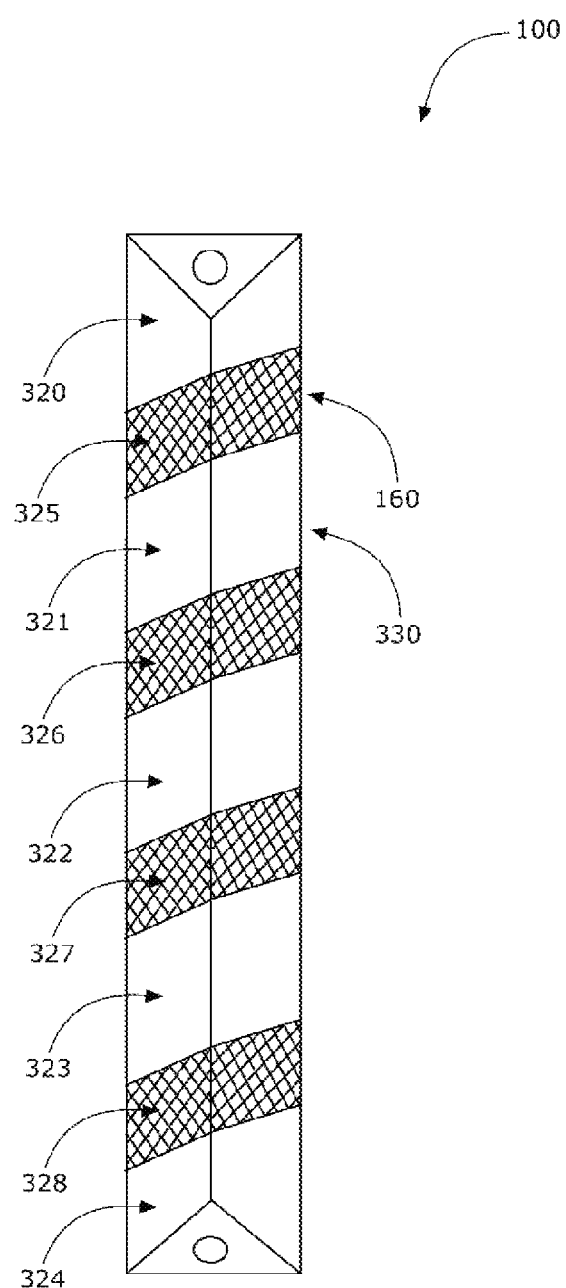
FIG. 4 is a top view illustrating the device for affecting water according of FIG. 1, to an embodiment of the present disclosure.

FIG. 4 is a top view of the device for affecting water of FIG. 1, according to an alternate embodiment of the present disclosure. According the alternate embodiment disclosed herein, extruded member 160 may include first-copper shell 320, second-copper shell 321, third-copper shell 322, fourth-copper shell 323, and fifth-copper 324 shell with first-mesh structure 325 situated between first-copper shell 320 and second-copper shell 321, second-mesh structure 326 situated between second-copper shell 321 and third-copper shell 322, third-mesh structure 327 situated between third-copper shell 322 and fourth-copper shell 323, and fourth-mesh structure 328 situated between fourth-copper shell 323 and fifth-copper shell 324 in structural and functional combination to create a plurality of interlaced mesh structures 329 in alternating configuration and having an outer copper shell 330 configured to permit potable water 20 (FIG. 1) to flow into and out of extruded member 160.

A device for affecting water 100 may be manufactured and provided for sale in a wide variety of sizes and shapes for a wide assortment of applications. Upon reading this specification, it should be appreciated that, under appropriate circumstances, considering such issues as design preference such as use of copper-strengthening alloys, user preferences, marketing preferences, cost, structural requirements, available materials, technological advances, etc., other kit contents or arrangements such as, for example, including more or less components, customized parts, different combinations and compositions for improving animal health, parts may be sold separately, etc., may be sufficient.

Figure 5:
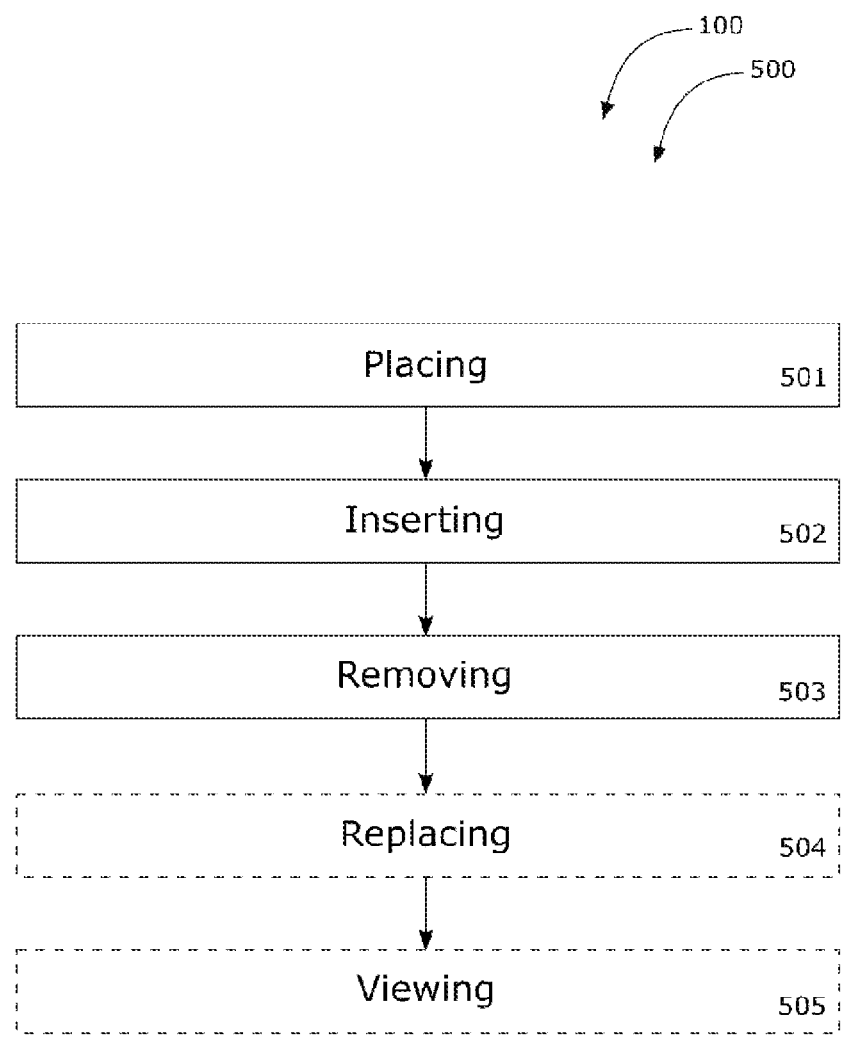
FIG. 5 is a flow diagram illustrating a method of use for the device for affecting water according to an embodiment of the present disclosure.

Referring now to FIG. 5 showing a flow diagram 550 illustrating method of use 500 for device for affecting water 100 according to an embodiment of the present invention of FIGS. 1-4. As shown, method of use 500 may comprise the steps of: step one 501, placing a mineral composition 222 in the mineral receptacle 221; step two 502, inserting the device for affecting water 100 in a standard disposable water bottle 5, and alternatively a reusable beverage vessel 15; step three 503, removing the device for affecting water 100 from the standard disposable water bottle 5, and alternatively the reusable beverage vessel 15, when use is no longer desired; step four 504, replacing at least one gemstone 231 with another at least one gemstone 231; and step five 505, viewing visual indicia 235 to induce a subliminal sentiment associated therewith.

It should be noted that steps 504 and 505 are optional steps and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for the device for affecting water (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A device for affecting water, the device comprising:
   a first-end;
   a second-end;
   a length from the first end to the second end;
   an extruded member at least partially made of copper extending between the first-end and the second-end, the extruded member having a substantially constant cross-sectional perimeter perpendicular to the length between the first-end and the second-end; the substantially constant cross-sectional perimeter having an isosceles triangle shape, the isosceles triangle shape having a base and a height; and
   a mineral receptacle, the mineral receptacle including an interlaced mesh having substantially the same cross-sectional perimeter and isosceles triangle shape as the extruded member, and configured to permit potable water to flow into and out of the mineral receptacle;
   wherein the first-end, the second-end, and the interlaced mesh structure are integrated with the extruded member.

2. The device of claim 1, further comprising a mineral composition, the mineral composition configured to leach mineral trace elements into the potable water when exposed to the potable water; and
   wherein the mineral receptacle is configured to be accessible by a user to removably-insert the mineral composition into the mineral receptacle.

3. The device of claim 2, wherein the mineral composition includes at least one of activated coconut carbon, ionic silver nanoparticle balls, tourmaline, shungite, silica-centered microclusters, and alternatively maifan stone.

4. The device of claim 2, wherein the mineral composition is selected from the group consisting of activated coconut carbon, ionic silver nanoparticle balls, tourmaline, shungite, silica-centered microclusters, and maifan stone.

5. The device of claim 1, wherein the first-end and second-end each include at least one aligned bipolar magnet.

6. The device of claim 1, wherein the extruded member is configured to be able to be removably-inserted within an inner volume of a standard disposable water bottle, and alternatively a reusable beverage vessel, without interfering with a closure mechanism of the standard disposable water bottle, and alternatively the reusable beverage vessel.

7. The device of claim 6, wherein the length of said extruded member is approximately 5 inches in length and the constant cross-sectional perimeter is approximately ¾ inches in width.

8. The device of claim 1, further comprising at least one gemstone, the at least one gemstone; and
   wherein the first-end includes a mounting interface configured to fixedly-attach, and alternatively to removably-couple, the at least one gemstone to the first end.

9. The device of claim 8, wherein the at least one gemstone includes at least one clear crystal quartz, amethyst, blue sodalite, green fluorite, rose crystal quartz, and alternatively calcite-gemstone.

10. The device of claim 8, wherein the at least one gemstone is selected from the group consisting of clear crystal quartz, amethyst, blue sodalite, green fluorite, rose crystal quartz, and calcite-gemstone.

11. The device of claim 1, wherein the extruded member has a solid cross section, the mineral receptacle located within the extruded member, and the mineral composition is sufficient to continue leaching the mineral trace elements into the potable water for an extended period of time.

12. The device of claim 1, wherein the first-end and the second-end are each configured to be hollow in cross section to provide a larger leaching surface area.

13. The device of claim 1, wherein the second-end includes visual indicia.

14. The device of claim 13, wherein the visual indicia includes at least one word and/or at least one image.

15. The device of claim 1, wherein the extruded member includes first-copper shell, a second-copper shell, a third-copper shell, a fourth-copper shell, and a fifth-copper shell with a first-mesh structure situated between the first-copper shell and the second-copper shell, a second-mesh structure situated between the second-copper shell and the third-copper shell, a third-mesh structure situated between the third-copper shell and the fourth-copper shell, and a fourth-mesh structure situated between the fourth-copper shell and the fifth-copper shell integrated to create a plurality of interlaced mesh structures in alternating configuration with a plurality of outer copper shells configured to permit potable water to flow into and out of said extruded member.

16. A device for affecting water, the device comprising:
   a first-end;
   a second-end;
   a length from the first end to the second-end;
   an extruded member at least partially made of copper extending between the first-end and the second-end, the extruded member having a substantially constant cross-sectional perimeter perpendicular to the length between the first-end and the second-end, the cross-sectional perimeter having an isosceles triangle shape, the isosceles triangle shape having a base and a height;

wherein said device further includes a mineral receptacle, the mineral receptacle including an interlaced mesh structure configured to permit potable water to flow into and out of the mineral receptacle;

wherein said first-end, said second-end, and said interlaced mesh structure are integrated with said extruded member;

wherein said device further includes a mineral composition, said mineral composition configured to leach mineral trace elements into said potable water when exposed to said potable water;

wherein said mineral receptacle is configured to be accessible by a user to removably-insert said mineral compositions into said mineral receptacle;

wherein said mineral composition includes at least one of activated coconut carbon, ionic silver nanoparticle balls, tourmaline, shungite, silica-centered microclusters, and alternatively maifan stone;

wherein said first-end and said second-end each include at least one aligned bipolar magnet;

wherein said extruded member is configured to be able to be removably-inserted within an inner volume of a standard disposable water bottle, and alternatively a reusable beverage vessel, without interfering with a closure mechanism of said standard disposable water bottle, and alternatively said reusable beverage vessel;

wherein said length of said extruded member is approximately 5 inches in length and the substantially constant cross-sectional perimeter is approximately ¾ inches in width; wherein said device further includes further includes at least one gemstone, the at least one gemstone;

wherein said first-end includes a mounting interface configured to fixedly-attach, and alternatively to removably-couple, said at least one gemstone to said first end;

wherein said at least one gemstone includes at least one clear crystal quartz, amethyst, blue sodalite, green fluorite, rose crystal quartz, and alternatively calcite-gemstone;

wherein said extruded member has a solid cross section, said mineral receptacle is located within said extruded member, said mineral composition is sufficient to continue leaching said mineral trace elements into said potable water for an extended period of time;

wherein said first-end and said second-end are each configured to be hollow in cross section to provide a larger leaching surface area;

wherein said second-end includes visual indicia;

wherein said visual indicia includes at least one word and/or at least one image;

wherein said extruded member includes first-copper shell, a second-copper shell, a third-copper shell, a fourth-copper shell, and a fifth-copper shell with a first-mesh structure situated between said first-copper shell and said second-copper shell, a second-mesh structure situated between said second-copper shell and said third-copper shell, a third-mesh structure situated between said third-copper shell and said fourth-copper shell, and a fourth-mesh structure situated between said fourth-copper shell and said fifth-copper shell integrated to create a plurality of interlaced mesh structures in alternating configuration with a plurality of outer copper shells configured to permit potable water to flow into and out of said extruded member.

17. A kit comprising:
the device for affecting water of claim 16, and
a set of instructions which include the step of placing the device in contact with water to be treated.

18. A method of using a device for affecting water comprising the steps of:
providing a device for affecting water, the device comprising:
a first-end;
a second-end;
a length from the first end to the second end;
an extruded member at least partially made of copper extending between the first-end and the second-end, the extruded member having a substantially constant cross-sectional perimeter perpendicular to the length between the first-end and the second-end; the substantially constant cross-sectional perimeter having an isosceles triangle shape, the isosceles triangle shape having a base and a height; and
a mineral receptacle, the mineral receptacle including an interlaced mesh having substantially the same cross-sectional perimeter and isosceles triangle shape as the extruded member, and configured to permit potable water to flow into and out of the mineral receptacle;
wherein the first-end, the second-end, and the interlaced mesh structure are integrated with the extruded member;
placing a mineral composition in the mineral receptacle;
inserting said device for affecting water in a standard disposable water bottle or a reusable beverage vessel; and
removing said device for affecting water from said bottle or vessel when use is no longer desired.

19. The method of claim 18 further comprising the steps of
replacing at least one gemstone with another at least one gemstone on a mounting interface of the device for affecting water; and
viewing a visual indicia on the device for affecting water wherein the visual indicia includes at least one word and/or at least one image.

* * * * *